United States Patent
Creaven et al.

(10) Patent No.: US 8,545,755 B2
(45) Date of Patent: Oct. 1, 2013

(54) SENSOR RELEASE MECHANISM FOR A TEST METER

(75) Inventors: John P. Creaven, Granger, IN (US); Russell J. Micinski, South Bend, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 1008 days.

(21) Appl. No.: 11/919,030

(22) PCT Filed: Apr. 25, 2006

(86) PCT No.: PCT/US2006/015848
§ 371 (c)(1),
(2), (4) Date: Oct. 18, 2007

(87) PCT Pub. No.: WO2006/116522
PCT Pub. Date: Nov. 2, 2006

(65) Prior Publication Data
US 2009/0042305 A1 Feb. 12, 2009

Related U.S. Application Data

(60) Provisional application No. 60/674,536, filed on Apr. 25, 2005.

(51) Int. Cl.
*G01N 21/00* (2006.01)
*G01N 35/00* (2006.01)
(52) U.S. Cl.
USPC .................. 422/64; 221/69; 422/63; 436/43
(58) Field of Classification Search
None
See application file for complete search history.

(56) References Cited

U.S. PATENT DOCUMENTS

| 4,911,344 | A |   | 3/1990 | Kahler ........................... 221/135 |
|---|---|---|---|---|
| 5,090,553 | A | * | 2/1992 | Focke ...................... 198/377.06 |
| 5,383,569 | A |   | 1/1995 | Muto |
| 5,489,414 | A |   | 2/1996 | Schreiber et al. ............... 422/64 |
| 5,510,266 | A |   | 4/1996 | Bonner et al. .................. 436/43 |
| 5,513,773 | A |   | 5/1996 | Cargill |

(Continued)

FOREIGN PATENT DOCUMENTS

EP 1 321 769 A1 6/2003
EP 1 475 630 A1 11/2004

(Continued)

OTHER PUBLICATIONS

Written Opinion corresponding to International Patent Application Serial No. PCT/2006/015848, European Patent Office, dated Aug. 22, 2006, 7 pages.

(Continued)

*Primary Examiner* — Dirk Bass
(74) *Attorney, Agent, or Firm* — Nixon Peabody LLP

(57) ABSTRACT

A sensor-dispensing instrument adapted to handle a sensor pack containing a plurality of sensors and to perform a test using one of the sensors. The sensor dispensing instrument includes an outer housing and a mechanical mechanism contained therein for rotating the sensor pack and ejecting one of the sensors from the sensor pack and through a sensor slot on the housing. The sensor dispensing instrument also includes a rotational-release wheel that is disposed on the outer housing of the sensor-dispensing instrument that is turnable to remove a sensor disposed in the sensor slot.

20 Claims, 7 Drawing Sheets

(56) References Cited

U.S. PATENT DOCUMENTS

| | | | |
|---|---|---|---|
| 5,575,403 A | 11/1996 | Charlton et al. | 221/31 |
| 5,630,986 A | 5/1997 | Charlton et al. | 422/64 |
| 5,906,366 A | 5/1999 | Chang | 271/124 |
| 5,941,414 A | 8/1999 | Kasper | 221/210 |
| 6,027,068 A * | 2/2000 | Lantsman | 242/564.4 |
| 6,534,017 B1 | 3/2003 | Bottwein et al. | 422/104 |
| 6,827,899 B2 | 12/2004 | Maisey et al. | 422/61 |
| 6,908,008 B2 | 6/2005 | Pugh | 221/135 |
| 6,997,343 B2 | 2/2006 | May et al. | 221/232 |
| 7,017,780 B2 * | 3/2006 | Renaud | 221/263 |
| 7,138,089 B2 | 11/2006 | Aitken et al. | 422/82.01 |
| 7,419,154 B2 | 9/2008 | Pelletier et al. | 271/124 |
| 7,552,843 B2 | 6/2009 | Kuriger et al. | |
| 7,585,464 B2 | 9/2009 | Amano et al. | |
| 2002/0057993 A1 | 5/2002 | Maisey et al. | 422/82.01 |
| 2002/0076349 A1 | 6/2002 | Aitken et al. | 422/58 |
| 2003/0031591 A1 | 2/2003 | Whitson et al. | 422/50 |
| 2003/0031599 A1 | 2/2003 | Brown | 422/100 |
| 2003/0036200 A1 | 2/2003 | Charlton | 436/43 |
| 2003/0089730 A1 | 5/2003 | May et al. | 221/232 |
| 2003/0116583 A1 | 6/2003 | Pugh | 221/268 |
| 2003/0121932 A1 * | 7/2003 | Wajda | 221/259 |
| 2003/0191415 A1 | 10/2003 | Moerman et al. | 600/584 |
| 2005/0017018 A1 * | 1/2005 | Von Falkenhausen et al. | 221/231 |
| 2007/0215634 A1 | 9/2007 | Levin | |
| 2007/0293790 A1 | 12/2007 | Bainczyk et al. | |
| 2008/0181818 A1 | 7/2008 | Ruan | |
| 2009/0042305 A1 | 2/2009 | Creaven et al. | |
| 2009/0230144 A1 | 9/2009 | Kuriger et al. | |

FOREIGN PATENT DOCUMENTS

| | | |
|---|---|---|
| EP | 1 500 925 A1 | 1/2005 |
| EP | 1949099 A2 | 7/2008 |
| EP | 1949099 B1 | 6/2010 |
| GB | 2 388 898 A | 11/2003 |
| JP | 9250998 | 9/1997 |
| TW | 200706850 A | 2/2007 |
| WO | WO 94/10558 | 5/1994 |
| WO | WO 02/18940 A2 | 3/2002 |
| WO | WO 02/078533 A2 | 10/2002 |
| WO | WO 03/082091 A2 | 10/2003 |
| WO | WO 03/082092 A1 | 10/2003 |
| WO | WO 03/083469 A2 | 10/2003 |
| WO | WO 2007/024272 A2 | 3/2007 |

OTHER PUBLICATIONS

International Search Report corresponding to International Patent Application Serial No. PCT/2006/05848, European Patent Office, dated Aug. 22, 2006, 3 pages.

* cited by examiner

SENSOR RELEASE MECHANISM FOR A TEST METER

CROSS-REFERENCE TO RELATED APPLICATIONS

This application claims priority to Application No. 60/674,536 filed on Apr. 25, 2005, which is incorporated by reference in its entirety.

FIELD OF THE INVENTION

The present invention relates generally to a fluid-monitoring system and, more particularly, to a new and improved meter or instrument for handling multiple sensors that are used in analyzing at least one analyte in a fluid contained therein (e.g. blood glucose, cholesterol).

BACKGROUND OF THE INVENTION

People suffering from various forms of diabetes routinely need to test their blood to determine the level of blood glucose. The results of such tests can be used to determine what, if any, insulin or other medication needs to be administered. In one type of blood glucose testing system, sensors are used to test a sample of blood.

Such a sensor may have a generally flat, rectangular shape with a front or testing end and a rear or contact end. The sensor contains biosensing or reagent material that will react with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor with the result that an electrical signal indicative of the blood glucose level in the blood being tested is supplied to contact areas located near the rear or contact end of the sensor.

To couple the electrical signals produced at the sensor contacts to monitoring equipment, the sensors need to be inserted into sensor holders prior to the sensor end being placed into the fluid being tested. The sensor holders have corresponding mating contact areas that become coupled to the contacts on the sensor when the sensor is inserted into the holder. Consequently, the holders act as an interface between the sensor and monitoring equipment that accumulates and/or analyzes the test results.

Prior to being used, the sensors typically need to be maintained at an appropriate humidity level so as to insure the integrity of the reagent materials in the sensor. Sensors can be packaged individually in tear-away packages so that they can be maintained at the proper humidity level. For instance, blister-type packaging methods could be used. In this connection, the packages can include desiccant material to maintain the proper humidity in the package. To use an individual sensor for testing blood glucose, the package must be opened by tearing the seal. Alternatively, some packages require the user to exert force against one side of the package resulting in the sensor bursting or rupturing the foil on the other side. As can be appreciated, the opening of these packages can be difficult. Moreover, once the package is opened, the user needs to be sure that the sensor is not damaged or contaminated as it is being placed into the sensor holder and used to test the blood sample.

Some users have experienced difficulties in the operation and/or manipulation of the prior art sensor instruments. For example, users with limited dexterity may find it difficult to remove a used sensor from the device. Because the used sensor contains blood or other fluids, the sensor should be disposed of immediately after the testing procedure is completed. Moreover, physical handling of the used sensor should be avoided to prevent or inhibit the spreading of blood-born diseases or other harmful contaminants. It is therefore desirable that the used sensor be removed from the device without being grasped or otherwise handled by the user.

One prior art technique involves discharging the used test sensor by sliding the slide latch away from the testing end of the device and simultaneously tipping the testing end of the device downwardly. This requires an awkward manipulation of the device that may be particularly difficult for users, particularly elderly users suffering from diabetes, which lack dexterity in their wrist, hand or fingers. As a result, many users may be tempted to grab the end of the used sensor to remove it from the device.

Another prior technique discloses a button that is depressed to release a previously used test sensor from the sensor-dispensing instrument. However, the release mechanism disclosed in such a prior technique relies primarily on the user tipping the end of the sensor-dispensing instrument down so that gravity will remove the test sensor. It has been found that some test sensors may not properly be ejected by such a prior release mechanism, such as if the test sensor has some contaminant on an exposed surface of the test sensor, such as some adhesive, static electricity may cause the test sensor to remain in the sensor-dispensing instrument, or the light weight of the test sensor makes it unlikely for the test sensor to be removed by gravity from the sensor-dispensing instrument. It is therefore desirable to have an improved sensor-dispensing instrument that utilizes an improved method of discharging used sensors.

SUMMARY OF THE INVENTION

According to one embodiment of the present invention, a sensor-dispensing instrument adapted to handle a sensor pack that contains a plurality of sensors, the sensor-dispensing instrument further adapted to perform a test using one of the plurality of sensors is provided. The sensor-dispensing instrument comprises an outer housing, a mechanical mechanism, an electronics assembly, a sensor actuator, and a rotational-release wheel. The outer housing has a front end and a rear end. The outer housing further has a sensor slot through which one of the sensors is disposed to conduct the test. The sensor slot is at the front of end of the outer housing. The mechanical mechanism includes an indexing disk for supporting and rotating the sensor pack, an indexing disk-drive arm for rotating the indexing disk, a knife-blade assembly, and a puller handle to move the indexing disk-drive arm and the knife-blade assembly. The electronics assembly performs the test and displays the test results. The sensor actuator is adapted to engage a sensor within the sensor slot, connect to contacts on the sensor, and transmit electrical signals between the sensor and the electronics assembly. The rotational-release wheel is generally disposed on the front end of the outer housing. The rotational-release wheel being turnable to remove the sensor from the sensor slot.

According to one method of the present invention, a method of operating a sensor-dispensing instrument adapted to handle a sensor pack containing a plurality of sensors, and the sensor-dispensing instrument further adapted to perform a test using one of the plurality of sensors is provided. The sensor-dispensing instrument comprises an outer housing that has a sensor slot disposed at a front end of the outer housing through which one of the sensors is disposed to conduct the test. The sensor-dispensing instrument further comprises a mechanical mechanism having an indexing disk for supporting and rotating the sensor pack, a movable disk-drive pusher, an indexing disk-drive arm mounted on the disk-drive pusher for rotating the indexing disk. A knife-blade assembly mounted on the disk-drive pusher for puncturing the foil covering and ejecting one of the sensors from the sensor cavity and through the sensor slot is also provided. The sensor-dispensing instrument additionally has a puller handle affixed to an end of the disk-drive pusher for moving the disk-drive pusher, the puller handle being moveable between a testing position adjacent to a rear end of the outer housing, an extended position spaced outwardly from the rear end of the outer housing, and a stand-by position located between the testing position and the extended position. The sensor-dispensing instrument further comprises a rotational-release wheel for removing a sensor in the sensor slot. The method pulls the puller handle from the stand-by position to the extended position so as to move the disk-drive pusher and cause the indexing disk-drive arm to rotate the indexing disk. The method pushes the puller handle from the extended position to the testing position so as to move the disk-drive pusher and cause the knife-blade assembly to puncture the foil covering and eject one of the sensors from the sensor cavity and through the sensor slot. The method performs the test by using the sensor disposed in the sensor slot. The user views the test results generated by the test on a display disposed on the outer housing. The user turns the rotational-release wheel to cause the rotational-release wheel to remove the sensor from the sensor slot.

The above summary of the present invention is not intended to represent each embodiment, or every aspect, of the present invention. Additional features and benefits of the present invention are apparent from the detailed description and figures set forth below.

DESCRIPTION OF ILLUSTRATED EMBODIMENTS

Figure 1:
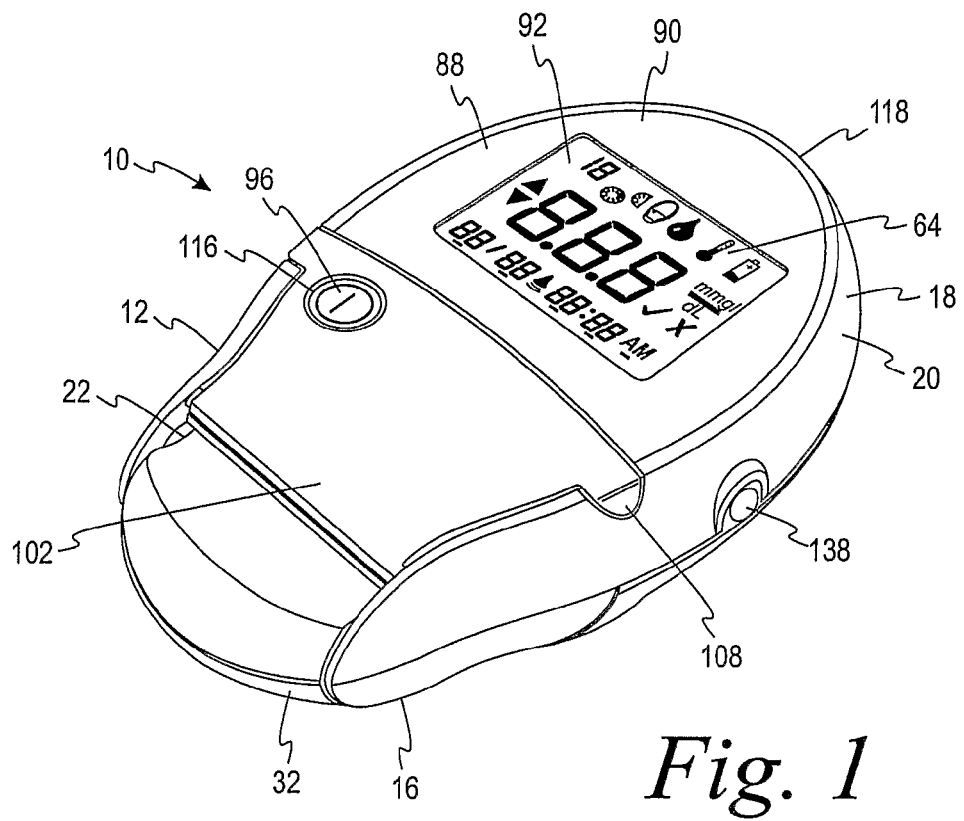
FIG. 1 is a top perspective view of a sensor-dispensing instrument according to one embodiment of the present invention.
Figure 2:
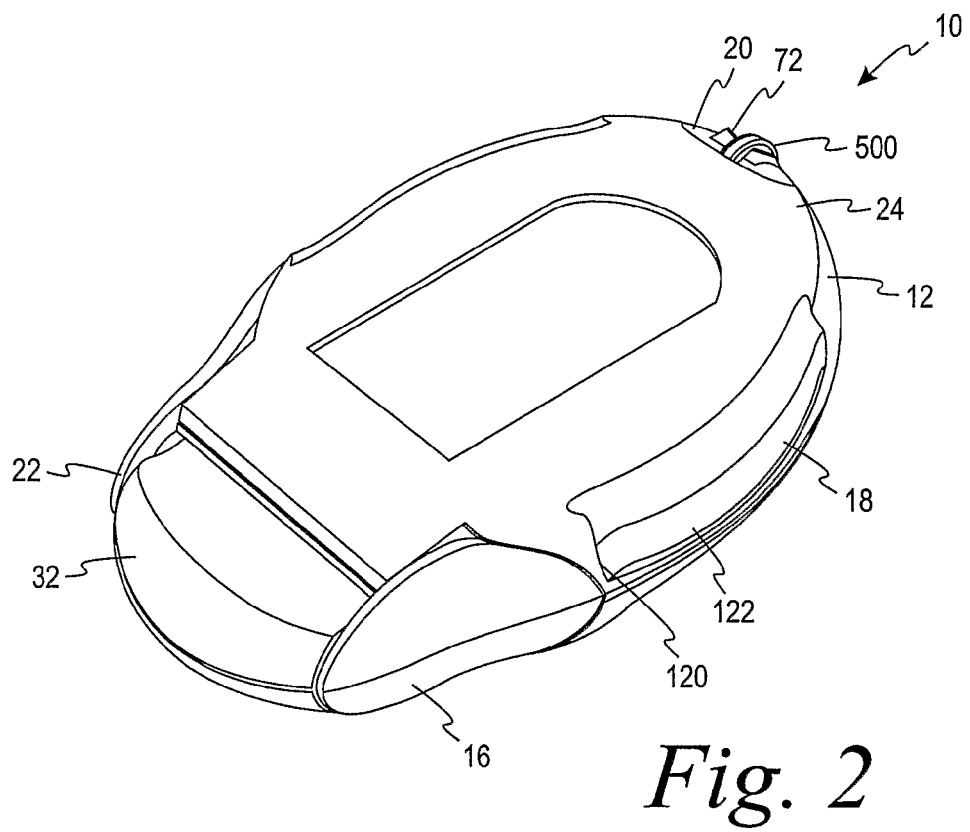
FIG. 2 is a bottom perspective view of the sensor-dispensing instrument of FIG. 1.
Figure 3:
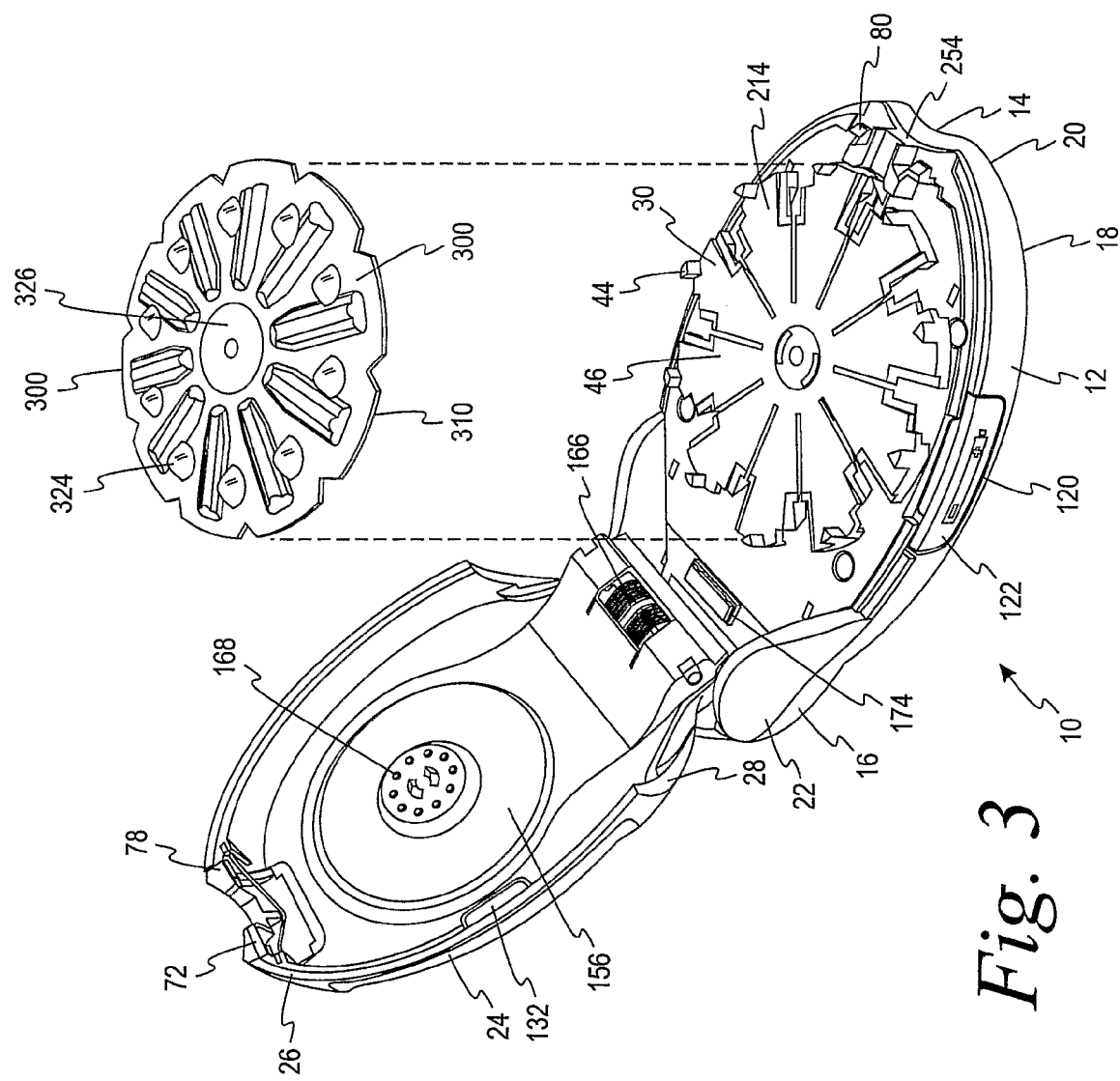
FIG. 3 is a perspective view of the sensor-dispensing instrument of FIG. 1 in the opened position showing the insertion of a sensor pack.

Referring now to FIG. 1 a sensor-dispensing instrument 10 is shown that may be used in determining concentration of at least one analyte in a fluid. Analytes that may be measured using the present invention include glucose, lipid profiles (e.g., cholesterol, triglycerides, LDL and HDL), microalbumin, hemoglobin $A_{1C}$, fructose, lactate, or bilirubin. Analytes that may be measured using the present invention include glucose, lipid profiles (e.g., cholesterol, triglycerides, LDL and HDL), microalbumin, hemoglobin $A_{1C}$, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, or other body fluids like ISF (interstitial fluid) and urine. The sensor-dispensing instrument 10 includes an outer housing 12 having an upper case 18 and a lower case 24, the lower case 24 pivoting on the upper case 18. The upper case 18 is pivotable with respect to the lower case 24 in a clamshell fashion so that a sensor pack 300 (see FIG. 3) can be positioned on an indexing disk 30 within the housing 12. With the sensor pack 300 so loaded in the housing 12, a puller handle 32 extending from a rear end 22 of the upper case 18 of the housing 12 can be moved to activate a disk-drive mechanism 34, to load a sensor 302 into a testing position on the front end 14 of the housing 12 (see FIG. 3).

Figure 5:
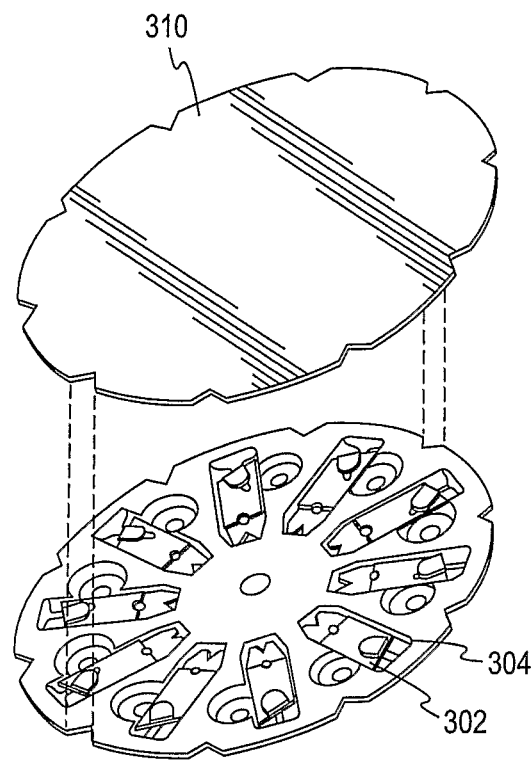
FIG. 5 is an exploded perspective view of the component parts of a sensor pack used with one embodiment of the present invention.
Figure 6:
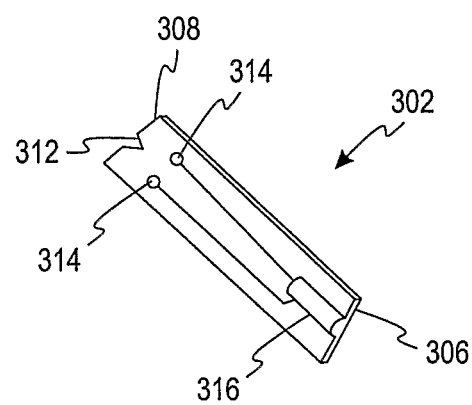
FIG. 6 is a perspective view of a test sensor used with one embodiment of the present invention.

As depicted in FIG. 5, the sensor pack 300 utilized by the sensor-dispensing instrument 10 is of the type described in U.S. Pat. No. 5,575,403, issued Nov. 19, 1996, entitled "Dispensing Instrument For Fluid Monitoring Sensors." In general, the sensor pack 300 is adapted to house a plurality of test sensors 302 with each of the test sensors 302 in a respective one of a plurality of separate sensor cavities 304. As shown in FIG. 6, each of the sensors 302 has a generally flat, rectangular shape extending from a front or testing end 306 to a back end 308. The front end 306 is angled so that it will puncture an unsevered portion of protective foil 310 overlying the sensor cavity 304 as the sensor 302 is being forced out of the sensor cavity 304 by a knife blade 36 (to be described below). The front end 306 is also adapted to be placed into a fluid (e.g. blood) that is being analyzed. The back end 308 of the sensor includes a small notch 312 that is engaged by the knife blade 36 as the knife blade 36 ejects the sensor 302 from the sensor cavity 304. Contacts 314 near the back end of the sensor 302 are adapted to mate with metal contacts on a sensor actuator 40 (to be described below) when the sensor 302 is in a testing position. As a result, the sensor 302 is coupled to the electronic circuitry on a circuit board assembly so that information generated in the sensor during testing can be stored, analyzed and/or displayed.

To operate the sensor-dispensing instrument 10, the puller handle 32 is first manually pulled from a standby position (FIG. 1) adjacent the rear end 16 of the housing 12 to an extended position away from the rear end 16 of the housing 12. The outward movement of the puller handle 32 causes the disk-drive mechanism 34 (FIGS. 4a and 4b) to rotate the sensor pack 300 and place the next sensor 302 in a standby position prior to being loaded into a testing position. The outward movement of the puller handle 32 also causes the sensor-dispensing instrument 10 to turn ON (i.e., the electronic circuitry on the circuit board assembly is activated).

As will be described in greater detail below, the disk-drive mechanism 34 includes a disk-drive pusher 48 on which an indexing disk-drive arm 50 is mounted (see FIGS. 4a and 4b). The indexing disk-drive arm 50 comprises a cam button 52 disposed at the end of a plate spring 54. The cam button 52 is configured to travel in one of a plurality of curvilinearly extending grooves 56 on the upper surface of the indexing disk 30. As the puller handle 32 is manually pulled from a standby position adjacent the rear end 16 of the housing 12 to an extended position away from the rear end 16 of the housing 12, the disk-drive pusher 48 is pulled laterally towards the rear end 22 of the upper case 18. This causes the cam button 52 on the indexing disk-drive arm 50 to travel along one of the curvilinearly extending grooves 56 so as to rotate the indexing disk 30. The rotation of the indexing disk 30 causes the sensor pack 300 to be rotated so that the next one of the sensor cavities 304 is placed in a standby position.

The puller handle 32 is then manually pushed inwardly from the extended position back past the standby position (FIG. 1) and into a testing position. The inward movement of the puller handle 32 causes the disk-drive mechanism 34 to remove a sensor 302 from the sensor pack 300 and place the sensor 302 into a testing position on the front end 14 of the housing 12.

As will be described in greater detail below, the disk-drive mechanism 34 includes a knife-blade assembly 58 that is pivotally mounted to the disk-drive pusher 48 (see FIGS. 4a and 4b). As the puller handle 32 is manually pushed from the extended position to the testing position, the disk-drive pusher 48 is pushed laterally towards the testing or front end 20 of the upper case 18. This causes the knife-blade assembly 58 to pivot downwardly so that a knife blade 36 on the end of the knife-blade assembly 58 pierces a portion of the protective foil 310 covering one of the sensor cavities 304 and engages the sensor 302 in the sensor cavity 304. As the disk-drive pusher 48 continues to move towards the front end 20 of the upper case 18, the knife-blade assembly 58 forces the sensor 302 out of the sensor cavity 304 and into a testing position at the front end 14 of the housing 12.

While the disk-drive pusher 48 is being pushed from the extended position to the testing position, the cam button 52 on the indexing disk-drive arm 50 travels along one of the radially extending grooves 60 to prevent the indexing disk 30 from rotating. Similarly, while the disk-drive pusher 48 is being pulled from the standby position to the extended position, the knife-blade assembly 58 is in a retracted position so as to not interfere with the rotation of the indexing disk 30.

As the sensor 302 is being ejected from the sensor cavity 304 and is being pushed into a testing position projecting out from the front end 14 of the housing 12, the sensor 302 engages a sensor actuator 40 and a rotational-release wheel 500 to thereby maintain the sensor 302 in the testing position. The sensor actuator 40 and the rotational-release wheel 500 engage the sensor 302 when the puller handle 32 is pushed past the standby position and into the testing position. The sensor actuator 40 couples the sensor 302 to an electronics assembly disposed in the upper case 18. The electronics assembly includes a microprocessor or the like for processing and/or storing data generated during the test procedure, and displaying the data on a liquid crystal display 64 of the sensor-dispensing instrument 10.

Once the fluid-analyzing test is completed, the rotational-release wheel 500 is rotated causing the sensor 302 to be expelled from the sensor-dispensing instrument 10. At this point, the user can turn the sensor-dispensing instrument 10 OFF by depressing the button 96 on the upper case 18, or by allowing the sensor-dispensing instrument 10 to automatically turn OFF pursuant to a timer on the electronics assembly.

Figure 4A:
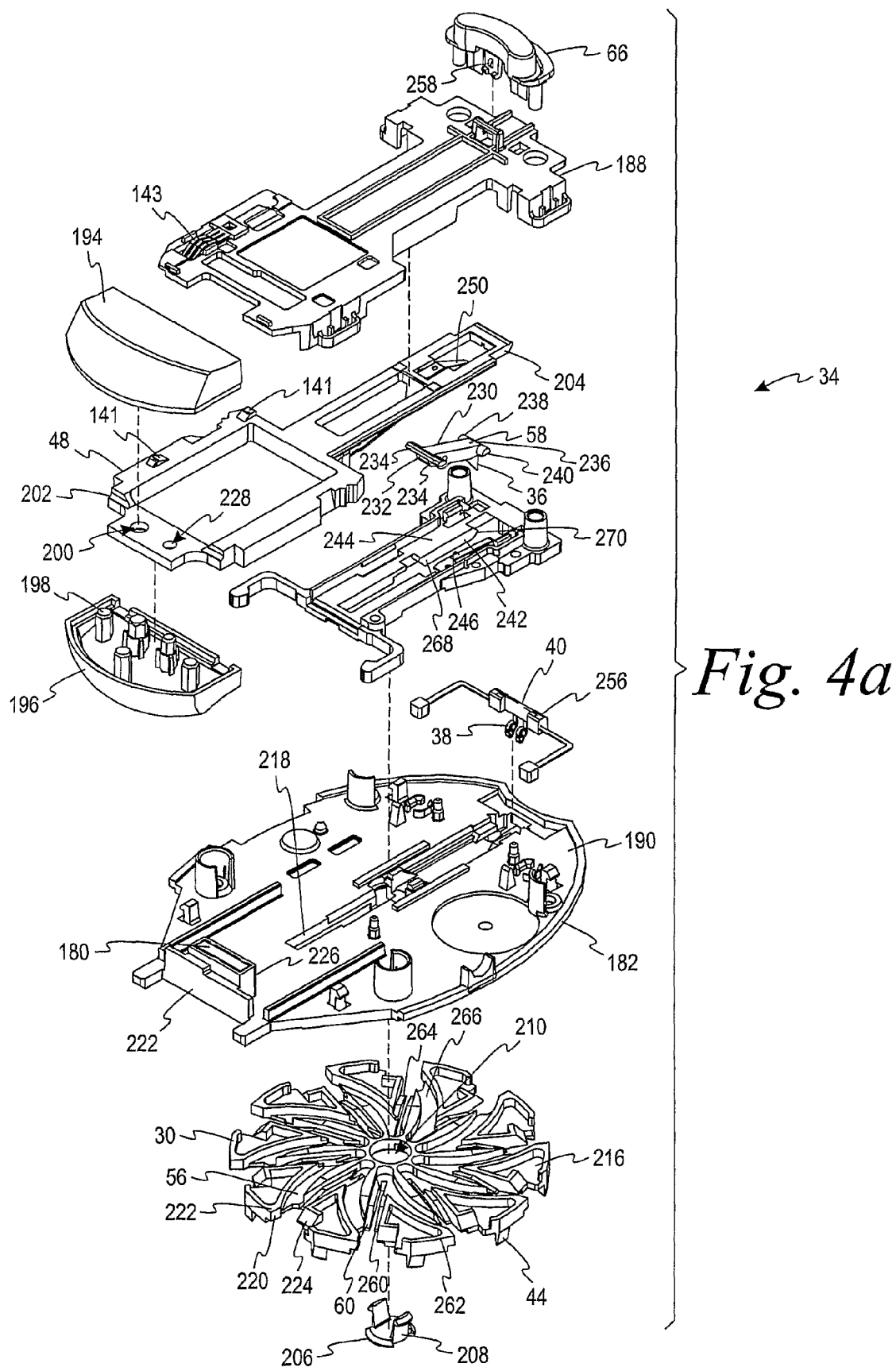
FIG. 4a is an exploded top perspective view of the component parts of a disk-drive mechanism and indexing disk sub-assembly of the sensor-dispensing instrument of FIG. 1.
Figure 4B:
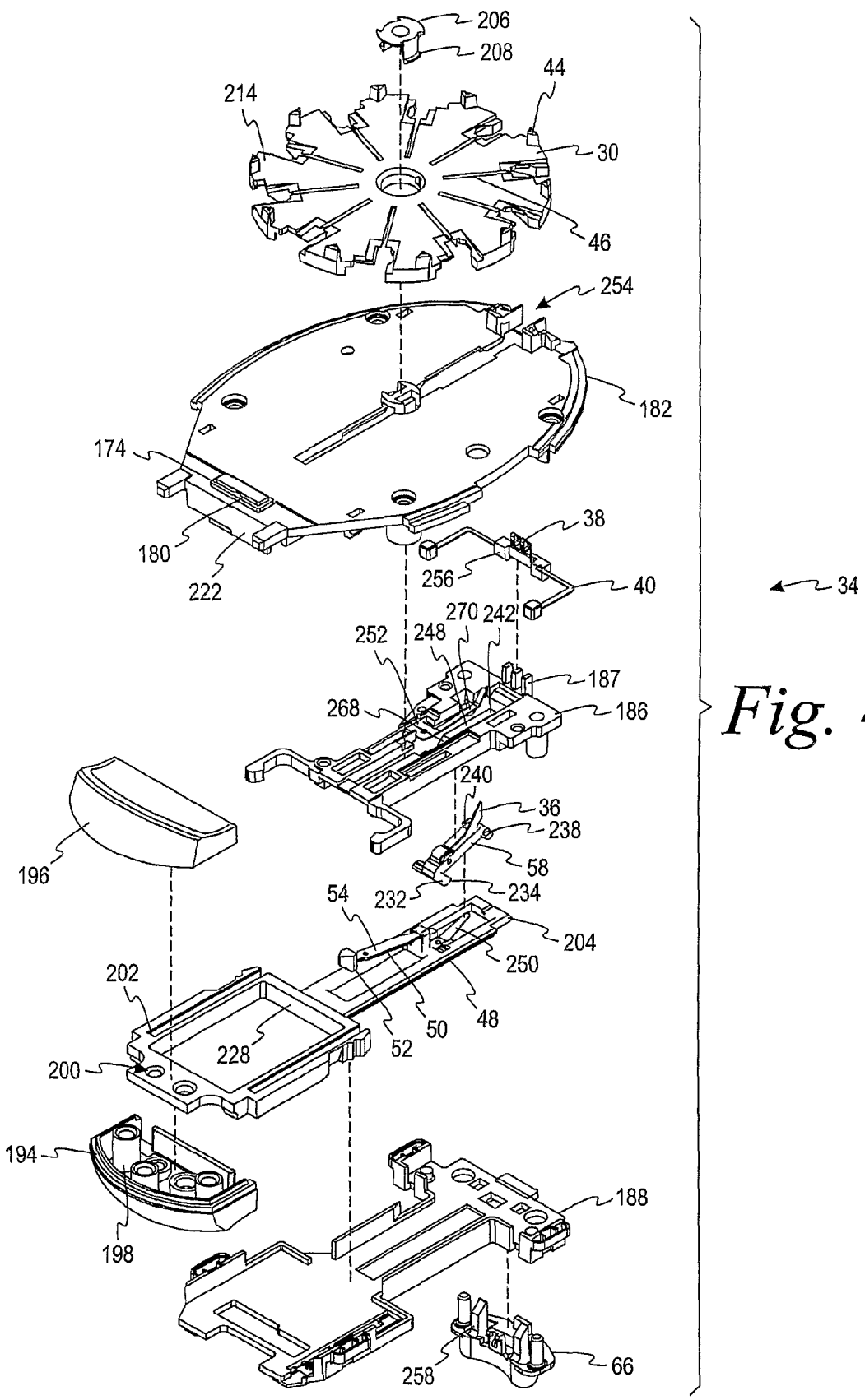
FIG. 4b is an exploded bottom perspective view of the component parts of a disk-drive mechanism and indexing disk sub-assembly of the sensor-dispensing instrument of FIG. 1.

As seen in FIGS. 4a-4b, the disk-drive mechanism 34 includes a knife-blade assembly 58 that is pivotally mounted to the disk-drive pusher 48. The knife-blade assembly 58 comprises a swing arm 230 having a first end 232 that is pivotally connected to the disk-drive pusher 48 by a pair of pivot pins 234. A knife blade 36 is connected to the second end 236 of the swing arm 230. The second end 236 of the swing arm 230 also includes a first cam follower 238 and a second cam follower 240, each in the shape of a transversely extending post. The first cam follower 238 is configured to follow a pathway formed on one side of the knife-blade assembly 58 by the guide block 182, the housing guide 186, and the cover mechanism 188. In particular, this pathway is formed by a cam projection 242 on the housing guide 186 that forms an upper pathway 244 between the cam projection 242 and the cover mechanism 188 and a lower pathway 246 between the cam projection 242 and the guide block 182. When the first cam follower 238 is disposed in the upper pathway 244, the knife blade 36 is in the retracted position. On the other hand, when the first cam follower 238 is disposed in the lower pathway 246, then the knife blade 36 is in the extended position. The upper pathway 244 and the lower pathway 246 are connected together at both ends of the cam projection 242 so as to form a continuous loop about which the first cam follower 238 can travel.

The second cam follower 240 engages a cam spring 248 (FIG. 4b) attached to the housing guide 186. As will be explained below, the cam spring 248 guides the knife-blade assembly 58 from the lower pathway 246 to the upper pathway 244 when the disk-drive pusher 48 is initially pulled rearward from standby position towards the extended position. The disk-drive pusher 48 also comprises a spring 250 for biasing the knife blade 36 towards the extended position when the disk-drive pusher 48 is initially pushed forward from the extended position towards the testing position. In the preferred embodiment shown, the spring 250 comprises a plate spring that presses against the upper side of the swing arm 230.

As the puller handle 32 is manually pushed from the extended position to the testing position, the disk-drive pusher 48 is pushed laterally towards the testing or front end 14 of the housing 12. As the disk-drive pusher 48 begins to move forward, the spring 250 biases the swing arm 230 downwardly towards the indexing disk 30 so that the first cam follower 238 engages a sloped surface 252 on the interior end 268 of the cam projection 242 and is forced into the lower pathway 246. This causes the knife blade 36 to assume an extended position whereby the knife blade 36 projects outwardly through a knife slot 46 in the indexing disk 30 to pierce the protective foil 310 covering one of the sensor cavities 304 and engage the notch 312 on the back end 308 of the sensor 302 contained therein. As the disk-drive pusher 48 continues to move towards the front end 20 of the upper case 18, the first cam follower 238 continues along the lower pathway 246, thereby causing the knife blade 36 to remain in the extended position projecting through the knife slot 46 so that it will travel along the knife slot 46 and push the sensor 302 forward out of the sensor cavity 304 and into a testing position at the front end 14 of the housing 12. As the sensor continues forward out of the sensor cavity and into the testing position the rotational-release wheel 500 contacts the sensor 302 to help to position the sensor in the testing position. The sensor 302 is in the testing position when the front end 306 of the sensor 302 projects out of the sensor opening 254 formed on the front end of the guide block 182. While in the testing position, the sensor 302 is prevented from being pushed back through the sensor opening 254 by the engagement of the knife blade 36 against the notch 312 on the back end 308 of the sensor 302.

As the sensor 302 reaches the testing position, the sensor actuator 40 and the rotational-release wheel 500 are in contact with the sensor 302. A pair of metal contacts 38 on the sensor actuator 40 to project into the sensor opening 254 on the guide block 182 and engage the contacts 314 on the sensor 302 for the glucose testing procedure. The metal contacts 38 apply a frictional force to the sensor 302 so that the sensor 302 does not prematurely fall out of the sensor opening 254 prior to completion of the testing procedure. In the embodiment shown, the metal contacts 38 are somewhat flexible and are made of stainless steel. The housing guide 186 includes support ribs 187 disposed adjacent to the metal contacts 38 so as to prevent or inhibit the metal contacts 38 from bending. As explained above, the metal contacts 38 permit the transmission of electrical signals between the sensor 302 and the electronics assembly during the testing procedure.

When the testing procedure is complete, a user turns the rotational-release wheel 500, typically using the user's thumb, to remove the sensor 302 from the testing device 10.

As mentioned above, when the disk-drive pusher 48 is pushed from the extended position towards the testing position, the cam button 52 on the indexing disk-drive arm 50 travels along one of the radially extending grooves 60 to prevent the indexing disk 30 and the sensor pack 300 from rotating. The radially extending groove 60 includes a sloped portion 260 that changes the depth of the groove 60. In particular, the sloped portion 260 decreases the depth of the radially extending groove 60 so that the middle portion of the radially extending groove 60 is shallower than the curvilinearly extending grooves 56. The radially extending groove 60 also comprises an inner step 262 near its inner end 264 (i.e., near the center of the indexing disk 30). The inner step 262 is formed along the juncture of the inner end 264 of the radially extending groove 60 and the inner end 266 of the curvilinearly extending groove 56. As the disk-drive pusher 48 is pushed from the extended position towards the testing position, the cam button 52 travels up the sloped portion 260 of the radially extending groove 60, past the inner step 262, and into the adjacent curvilinearly extending groove 56. The biasing force of the plate spring 54 of the indexing disk-drive arm 50 causes the cam button 52 to travel downwardly past the inner step 262. The inner step 262 prevents the cam button 52 from re-entering the radially extending groove 60 when the direction of travel of the disk-drive pusher 48 is reversed (as explained above in connection with the outward movement of the disk-drive pusher 48).

As the disk-drive pusher 48 reaches the testing position, the first cam follower 238 passes the exterior end 270 of the cam projection 242. At the same time, the second cam follower 240 passes over the end of the cam spring 248, which retracts upwardly and out of the way as the first cam follower 238 nears the exterior end 270 of the cam projection 242. Once the first cam follower 238 has passed the end of the cam spring 248, the cam spring 248 moves downwardly so as to engage and guide the second cam follower 240 upwardly when the direction of travel of the disk-drive pusher 48 is reversed and pulled outward towards the extended position. In particular, when the disk-drive pusher 48 is subsequently pulled outward towards the extended position, the cam spring 248 guides the second cam follower 240 upwardly so that the first cam follower 238 enters the upper pathway 244 and the knife blade 36 is retracted.

As explained above, the disk-drive pusher 48 is pulled outwardly to initiate the testing procedure. During the outward motion of the disk-drive pusher 48, the cam button 52 on the indexing disk-drive arm 50 travels along one of the curvilinearly extending grooves 56 so as to rotate the indexing disk 30. During this outward motion, the first cam follower 238 on the knife-blade assembly 58 travels along the upper pathway 244. As a result, the knife blade 36 is retracted from the knife slot 46 on the indexing disk 30 so that the indexing disk 30 is free to rotate in response to action of the cam button 52 in the curvilinearly extending groove 56. As the disk-drive pusher 48 reaches the fully extended position, the first cam follower 238 passes the interior end 268 of the cam projection 242 and is guided into the lower pathway 246 by the biasing force of the spring 250 on the swing arm 230 of the knife-blade assembly 58.

The following is a brief description of the operation of the sensor-dispensing instrument 10. First, the puller handle 32 is manually pulled from a standby position (FIG. 1) adjacent the rear end 16 of the housing 12 to an extended position away from the rear end 16 of the housing 12. The outward movement of the puller handle 32 causes the sensor-dispensing instrument 10 to turn ON. The outward movement of the puller handle 32 also causes the cam button 52 on the indexing disk-drive arm 50 to travel along one of the curvilinearly extending grooves 56 on the upper surface 216 of the indexing disk 30 so as to rotate the indexing disk 30 $\frac{1}{10}^{th}$ of a complete rotation. The rotation of the indexing disk 30 causes the sensor pack 300 to be rotated so that the next one of the sensor cavities 304 is placed in a standby position aligned with the testing end 14 of the housing 12. At the same time, the knife-blade assembly 58 is retracted and moved towards the center of the indexing disk 30.

Next, the puller handle 32 is manually pushed inwardly from the extended position back past the standby position and into a testing position. Tie inward movement of the puller handle 32 causes the knife-blade assembly 58 to pivot downwardly so that a knife blade 36 pierces a portion of the protective foil 310 covering the sensor cavity 304 in the standby position and engages the sensor 302 in the sensor cavity 304. As the puller handle 32 continues to move back towards the housing 12, the knife-blade assembly 58 forces the sensor 302 out of the sensor cavity 304 and into a testing position at the front end 14 of the housing 12. At the same time, the cam button 52 on the indexing disk-drive arm 50 travels along one of the radially extending grooves 60 to prevent the indexing disk 30 from rotating.

As the sensor 302 is being ejected from the sensor cavity 304 and is being pushed into a testing position projecting out from the front end 14 of the housing 12, the sensor 302 engages a sensor actuator 40 and a rotational-release wheel 500 to thereby maintain the sensor 302 in the testing position. The sensor actuator 40 and the rotational-release wheel 500 engage the sensor 302 when the puller handle 32 is pushed past the standby position and into the testing position. The sensor actuator 40 additionally couples the sensor 302 to the electronics assembly. The front end 306 of the sensor is then inserted into a drop of fluid, such as blood, to be tested, whereby the fluid is analyzed by the electronics assembly. The results of the analysis are then displayed on the liquid crystal display 64 of the sensor-dispensing instrument 10.

Once the analysis of the fluid is complete, the rotational-release wheel 500 is turned to remove the sensor 302 from the sensor-dispensing instrument 10.

Figure 7:
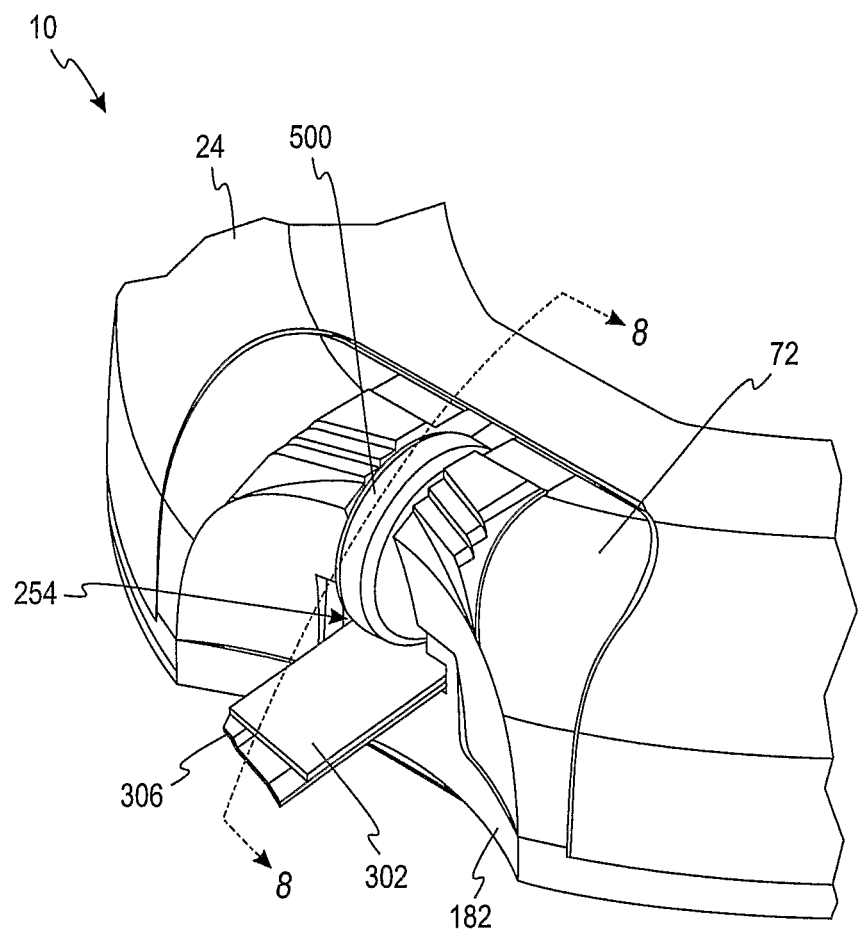
FIG. 7 is an enlarged partial perspective view of a front end of the sensor-dispensing instrument of FIG. 1.
Figure 8A:
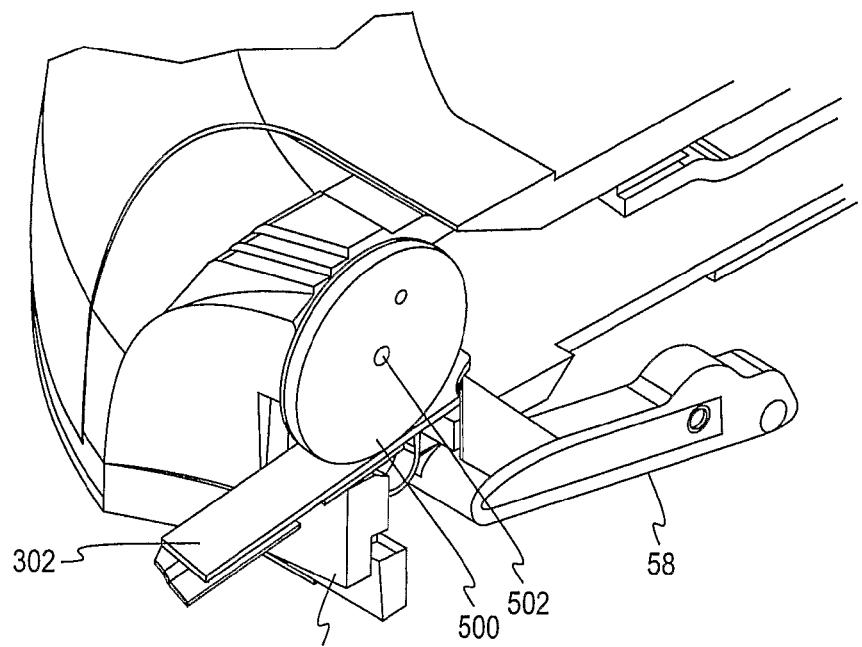
FIG. 8a is an enlarged partial cross-sectional perspective view of the front end of the sensor-dispensing instrument of FIG. 1 taken along line 8-8 of FIG. 7.
Figure 8B:
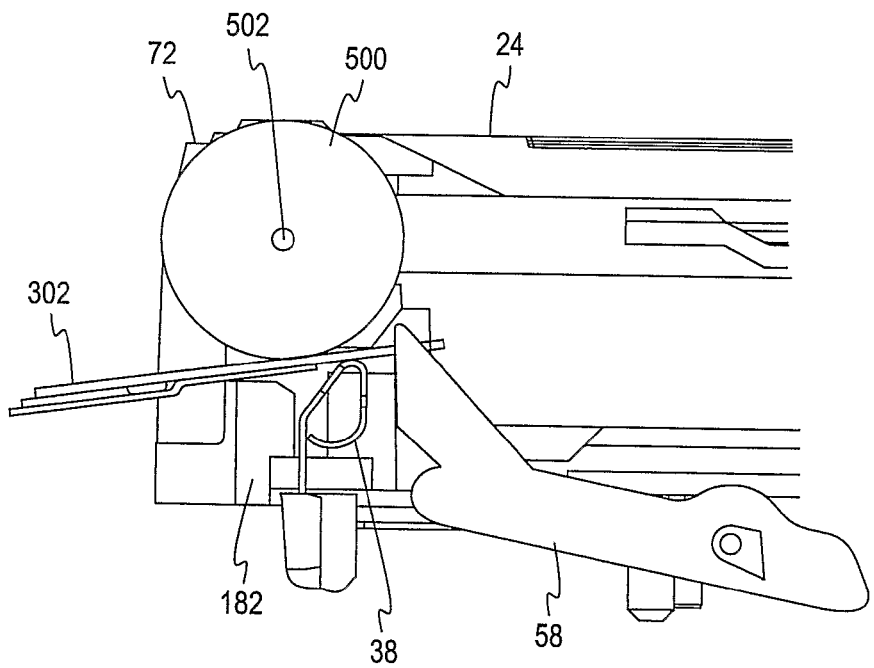
FIG. 8b is an enlarged partial cross-sectional side view of the front end of the sensor-dispensing instrument of FIG. 1 taken along line 8-8 of FIG. 7.

Turning now to FIGS. 7, 8a, and 8b, enlarged partial views of the sensor-dispensing instrument 10 are shown such that the rotational-release wheel 500 is depicted in greater detail.

As seen in FIG. 7, the rotational-release wheel 500 is mounted to the lower case 24. In some embodiments it is contemplated that the rotational wheel may be mounted to the latch of the lower case. The rotational-release wheel 500 may be coated with a material to increase the friction between the rotational-release wheel 500 and the sensor 302. Non-limiting examples of such a material to increase friction between the rotational-release wheel 500 and the test sensor 302 are rubber, silicone, or other polymeric materials. Additionally the rotational-release wheel 500 may be metal with a serrated surface to better grip the test sensors. The sensor 302 protrudes through the sensor opening 254 of the guide block 182.

FIG. 8a shows a partial section view taken through line 8-8 of FIG. 7. The rotational-release wheel 500 is mounted to the lower case 24 via an axle 502. The axle 502 passes through the rotational-release wheel to secure the rotational-release wheel in place, yet still allow the rotational-release wheel 500 to rotate about the axle 502. The knife blade assembly 58 is additionally shown positioning the sensor 302 through the sensor opening 254. As shown in FIG. 8b, the electrical contacts 38 are fixed in placed and interact with the rotational-release wheel 500 to secure the test sensor 302. As the test sensor 302 is dispensed from the sensor pack 300 the test sensor 302 contacts the electrical contacts 38 and the rotational-release wheel 500 and is secured between the electrical contacts 38 and the rotational-release wheel 500. Once testing is complete, the user turns the rotational-release wheel 500 to remove the test sensor 302 from the sensor-dispensing instrument 10.

While the present invention has been described in connection with a test dispensing instrument that contains multiple test sensors, it is further contemplated that the rotational-release wheel may be used with a testing device adapted to only contain a single test sensor.

Alternative Embodiment A

A sensor-dispensing instrument adapted to handle a sensor pack containing a plurality of sensors, each of the plurality of sensors being disposed in a sensor cavity on the sensor pack and enclosed by a protective covering, the sensor-dispensing instrument further adapted to perform a test using one of the plurality of sensors, the sensor-dispensing instrument comprising:

an outer housing having a front end and a rear end, the outer housing further having a sensor slot through which one of the sensors is disposed to conduct the test, the sensor slot being disposed at the front end of the outer housing;

a mechanical mechanism generally disposed within the outer housing, the mechanical mechanism including an indexing disk for supporting and rotating the sensor pack, an indexing disk-drive arm for rotating the indexing disk, a knife-blade assembly for puncturing the protective covering and ejecting one of the sensors from the sensor cavity and through the sensor slot, and a puller handle for moving the indexing disk-drive arm and the knife-blade assembly;

an electronics assembly generally disposed in the outer housing, the electronic assembly adapted to perform the test and to display test results;

a sensor actuator generally disposed adjacent to the sensor slot, the sensor actuator adapted to engage with a sensor disposed in the sensor slot, to connect to contacts on the sensor, and to transmit electrical signals between the sensor and the electronics assembly; and a rotational-release wheel generally disposed on the front end of the outer housing, the rotational-release wheel being turnable to remove the sensor disposed in the sensor slot.

Alternative Embodiment B

The sensor-dispensing instrument of Alternative Embodiment A wherein an axle connects the rotational-release wheel to the housing.

Alternative Embodiment C

The sensor-dispensing instrument of Alternative Embodiment B wherein the axle is mounted to a lower case of the outer housing.

Alternative Embodiment D

The sensor-dispensing instrument of Alternative Embodiment C wherein the axle is mounted to a latch connecting an upper case to the lower case of the outer housing.

Alternative Embodiment E

The sensor-dispensing instrument of Alternative Embodiment A wherein the puller handle is moveable between a testing position adjacent to the rear end of the outer housing and an extended position spaced outwardly from the rear end of the outer housing, and wherein the puller handle is moved from the testing position to the extended position to rotate the indexing disk, and is moved from the extended position to the testing position to puncture the protective covering and eject one of the sensors from the sensor cavity and through the sensor slot.

Alternative Embodiment F

The sensor-dispensing instrument of Alternative Embodiment A wherein the mechanical mechanism further comprises a movable disk-drive pusher, the indexing disk-drive arm and said knife-blade assembly being mounted on the disk-drive pusher, and the puller handle being affixed to a rear end of the disk-drive pusher.

Alternative Embodiment G

The sensor-dispensing instrument of Alternative embodiment A, wherein the sensor actuator is fixed within the outer housing.

Alternative Embodiment H

The sensor-dispensing instrument of Alternative Embodiment A wherein the sensor actuator is fixed within the outer housing.

Alternative Embodiment I

The sensor-dispensing instrument of Alternative Embodiment A wherein the rotational-release wheel projects outwardly from the surface of the outer housing, the rotational-release wheel being rotated to remove the sensor disposed in the sensor slot.

Alternative Embodiment J

The sensor-dispensing instrument of Alternative Embodiment A wherein the rotational-release wheel and the sensor actuator are adapted to secure the sensor disposed in the sensor slot.

Alternative Process K

A method of operating a sensor-dispensing instrument adapted to handle a sensor pack containing a plurality of sensors, each of the plurality of sensors being disposed in a sensor cavity on the sensor pack and enclosed by a protective covering, and the sensor-dispensing instrument further adapted to perform a test using one of the plurality of sensors, the sensor-dispensing instrument comprising an outer housing having a sensor slot disposed at a front end of the outer housing through which one of the sensors is disposed to conduct the test, the sensor-dispensing instrument further comprising a mechanical mechanism having an indexing disk for supporting and rotating the sensor pack, a movable disk-drive pusher, an indexing disk-drive arm mounted on the disk-drive pusher for rotating the indexing disk, a knife-blade assembly mounted on the disk-drive pusher for puncturing the foil covering and ejecting one of the sensors from the sensor cavity and through the sensor slot, and a puller handle affixed to an end of the disk-drive pusher for moving the disk-drive pusher, the puller handle being moveable between a testing position adjacent to a rear end of the outer housing, an extended position spaced outwardly from the rear end of the outer housing, and a stand-by position located between the testing position and the extended position, and the sensor-dispensing instrument further comprising a rotational-release wheel for removing the sensor from the sensor slot, the method comprising the acts of:

pulling the puller handle from the stand-by position to the extended position so as to move the disk-drive pusher and cause the indexing disk-drive arm to rotate the indexing disk;

pushing the puller handle from the extended position to the testing position so as to move the disk-drive pusher and cause the knife-blade assembly to puncture the protective covering and eject one of the sensors from the sensor cavity and through the sensor slot;

performing the test by using the sensor disposed in the sensor slot; and turning the rotational-release wheel so as to cause the rotational-release wheel to remove the sensor from the sensor slot.

Alternative Process L

The method of Alternative Process K wherein the turning the rotational-release wheel comprises rotating the rotational-release wheel about an axle secured in the outer housing.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A sensor-dispensing instrument adapted to handle a plurality of sensors, the sensor-dispensing instrument further adapted to perform a test using one of the plurality of sensors, the sensor-dispensing instrument comprising:

an outer housing having a front end and a rear end, the outer housing further having a sensor slot through which one of the sensors is disposed to conduct the test;

an electronics assembly generally disposed in the outer housing, the electronic assembly adapted to perform the test and to display test results;

a sensor actuator disposed generally adjacent to the sensor slot, the sensor actuator adapted to engage with a sensor disposed in the sensor slot, to connect to contacts on the sensor, and to transmit electrical signals between the sensor and the electronics assembly; and a rotational-release wheel positioned to engage the sensor in the sensor slot and to hold the sensor in contact with the sensor actuator during the test, the rotational-release wheel at least partially projecting outwardly from the outer housing, the rotational-release wheel being turnable to disengage the sensor from the sensor actuator and to remove the sensor disposed in the sensor slot.

2. The sensor-dispensing instrument of claim 1, wherein an axle connects the rotational-release wheel to the housing.

3. The sensor-dispensing instrument of claim 2, wherein the axle is mounted to a lower case of the outer housing.

4. The sensor-dispensing instrument of claim 3, wherein the axle is mounted to a latch connecting an upper case to the lower case of the outer housing.

5. The sensor-dispensing instrument of claim 1, further comprising an actuation member disposed generally within the outer housing, the actuation member being moveable between a testing position and an extended position, and wherein the actuation member is moved from the extended position to the testing position to eject one of the sensors through the sensor slot.

6. The sensor-dispensing instrument of claim 1, further comprising a mechanism disposed generally within the outer housing, the mechanism including an indexing disk for supporting and rotating the plurality of sensors, an indexing support for rotating the indexing disk, the ejecting mechanism, and an actuation member for moving the indexing support and the ejecting mechanism.

7. The sensor-dispensing instrument of claim 1, wherein the sensor actuator is fixed within the outer housing.

8. The sensor-dispensing instrument of claim 1, wherein the ejecting mechanism is a knife-blade assembly.

9. The sensor-dispensing instrument of claim 1, wherein the rotational-release wheel is coated with a material to increase frictional contact between the rotational-release wheel and the sensor disposed in the sensor slot.

10. The sensor-dispensing instrument of claim 9, wherein the material includes rubber, silicone, polymeric material, or any combination thereof.

11. A method of operating a sensor-dispensing instrument adapted to handle a plurality of sensors, the sensor-dispensing instrument further adapted to perform a test using one of the plurality of sensors, the method comprising the acts of:

providing a sensor-dispensing instrument including an outer housing and a rotational-release wheel, the outer housing having a sensor slot through which one of the sensors is disposed to conduct the test, the rotational-release wheel being positioned to engage the sensor in the sensor slot and to hold the sensor in contact with a sensor actuator of the sensor-dispensing instrument during the test, the rotational-release wheel at least partially projecting outwardly from the outer housing, an ejecting mechanism for ejecting one of the sensors through the sensor slot, and an actuation member, the actuation member being moveable between a testing position, an extended position, and a stand-by position being located between the testing position and the extended position;

moving the actuation member from a first position to a second position so as to cause the ejecting mechanism to eject one of the sensors through the sensor slot;

performing the test by using the sensor disposed in the sensor slot; and turning the rotational-release wheel to disengage the sensor from the sensor actuator and to remove the sensor from the sensor slot.

12. The method of claim 11, wherein the turning the rotational-release wheel comprises rotating the rotational-release wheel about an axle secured in the outer housing.

13. The method of claim 11, wherein an axle connects the rotational-release wheel to the housing.

14. The method of claim 13, wherein the axle is mounted to a lower case of the outer housing.

15. The method of claim 14, wherein the axle is mounted to a latch connecting an upper case to the lower case of the outer housing.

16. The method of claim 11, wherein the ejecting mechanism is a knife-blade assembly.

17. A method of operating a sensor-dispensing instrument adapted to handle a plurality of sensors and the sensor-dispensing instrument further adapted to perform a test using one of the plurality of sensors, the method comprising the acts of:

provoding a sensor-dispensing instrument including an outer housing, an electronics assembly, a sensor actuator, and a rotational-release wheel, the outer housing having a sensor slot through which one of the sensors is disposed to conduct the test, the rotational-release wheel being positioned to engage the sensor in the sensor slot and to hold the sensor in contact with the sensor actuator during the test, the rotational-release wheel at least partially projecting outwardly from the outer housing, an ejecting mechanism for ejecting one of the sensors through the sensor slot, and an actuation member for moving the ejecting assembly, the actuation member being moveable between a testing position, an extended position, and a stand-by position being located between the testing position and the extended position, the electronics assembly generally disposed in the outer housing, the electronic assembly adapted to perform the test and to display test results, the sensor actuator being disposed generally adjacent to the sensor slot, the sensor actuator being adapted to engage with a sensor disposed in the sensor slot, to connect to contacts on the sensor, and to transmit electrical signals between the sensor and the electronics assembly;

moving the actuation member from the stand-by position to the extended position;

moving the actuation member from the extended position to the testing position so as to cause the ejecting mechanism to eject one of the sensors through the sensor slot;

performing the test by using the sensor disposed in the sensor slot; and turning the rotational-release wheel to disengage the sensor from the sensor actuator and to remove the sensor from the sensor slot.

18. The method of claim 17, wherein the turning the rotational-release wheel comprises rotating the rotational-release wheel about an axle secured in the outer housing.

19. The method of claim 17, wherein the rotational-release wheel and the sensor actuator are adapted to secure the sensor disposed in the sensor slot.

20. The method of claim 17, wherein the ejecting mechanism is a knife-blade assembly, the knife-blade assembly further assisting in puncturing the protective covering.

\* \* \* \* \*